United States Patent [19]

Hill et al.

[11] Patent Number: 5,364,647
[45] Date of Patent: Nov. 15, 1994

[54] POWDERED PREPARATIONS OF SURFACE ACTIVE ALKYLGLYCOSIDES

[75] Inventors: Karlheinz Hill, Erkrath; Franz Foerg, Langenfeld; Hermann Koerner, Duesseldorf; Josef Penninger, Hilden, all of Germany

[73] Assignee: Henkel Kommanditgesellschaft auf Aktien, Duesseldorf, Germany

[21] Appl. No.: 171,378

[22] PCT Filed: Jul. 26, 1990

[86] PCT No.: PCT/EP90/01226

§ 371 Date: Feb. 4, 1992

§ 102(e) Date: Feb. 4, 1992

[87] PCT Pub. No.: WO91/02046

PCT Pub. Date: Feb. 21, 1991

Related U.S. Application Data

[63] Continuation of Ser. No. 828,864, Feb. 4, 1992, abandoned.

[51] Int. Cl.$^5$ .................... C11D 1/66; A61K 7/16
[52] U.S. Cl. .................... 424/490; 424/493; 424/498; 424/49; 424/57; 428/403; 428/404
[58] Field of Search ............ 424/489, 490, 493, 502, 424/49, 57, 498; 536/18.6; 428/402, 403, 404

[56] References Cited

U.S. PATENT DOCUMENTS

| | | | |
|---|---|---|---|
| 3,957,695 | 5/1976 | Davies et al. | 252/532 |
| 4,051,046 | 9/1977 | Diehl et al. | 252/8.6 |
| 4,162,236 | 7/1977 | Feierstein et al. | 252/558 |
| 4,536,319 | 8/1985 | Payne | 252/174.17 |
| 4,830,784 | 5/1989 | Meffert et al. | 252/547 |

FOREIGN PATENT DOCUMENTS

WO87/02053  4/1987  WIPO.

*Primary Examiner*—John Kight, III
*Assistant Examiner*—Jeffrey Culpeper Mullis
*Attorney, Agent, or Firm*—Ernest G. Szoke; Wayne C. Jaeschke; Daniel S. Ortiz

[57] ABSTRACT

Powder-form preparations of surface-active alkyl glycosides contain 5 to 65% by weight of a surface-active alkyl glycoside and 35 to 95% by weight of an inert inorganic support. They are produced by mixing the crude product obtained in the industrial production of the alkyl glycosides with water and an inorganic particulate support, for example silica, chalk or sodium chloride, and drying the resulting mixture. Preferred powder-form preparations contain 20 to 50% by weight of the alkyl glycoside and 50 to 80% by weight of an inert inorganic support.

5 Claims, No Drawings

POWDERED PREPARATIONS OF SURFACE ACTIVE ALKYLGLYCOSIDES

This application is a continuation, of application Ser. No. 07/828,864 filed on Feb. 4, 1992, now abandoned.

This invention relates to free-flowing powder-form preparations of surface-active alkyl glycosides and to a process for their production by drying of an aqueous mixture of alkyl glycoside and inert particulate support materials.

Surface-active alkyl glycosides in the context of the present invention are the reaction products of sugars and aliphatic primary alcohols preferably containing 8 to 22 carbon atoms. The sugar components, which are referred to hereinafter as glycoses, are preferably glucose and also fructose, mannose, galactose, talose, gulose, allose, altrose, idose, arabinose, xylose, lyxose, ribose and mixtures thereof.

The acetalization products of glucose with fatty alcohols obtainable, for example, from natural fats and oils by known methods, i.e. with linear, primary, saturated and unsaturated $C_{8-22}$ alcohols, are preferred by virtue of their ready availability and their good performance properties. Accordingly, the invention preferably relates to these types of alkyl glycosides which are also referred to hereinafter as alkyl glucosides.

Where they are produced by known methods for example in accordance with U.S. Pat. No. 3,839,318 or EP 132 046 A1, alkyl glycosides are accompanied by different residual quantities of unreacted starting products, among which the fatty alcohol is particularly troublesome in many applications. The crude acetalization products are solid, solidified melts which cannot be cast or dispersed at normal temperature.

In one particularly preferred production process, glucose is acetalized with fatty alcohol, water being continuously distilled off from the mixture under reduced pressure. In this production process, which is described in detail in German patent application P 38 33 780.0, the crude alkyl glucoside is obtained in the form of a solidified melt containing approximately 63% by weight fatty alkyl monoglucoside, 15% by weight fatty alkyl diglucoside, 6% by weight fatty alkyl triglucoside, 3% by weight alkyl tetraglucoside, 6% by weight polyglucose and 2 to 4% by weight residual fatty alcohol. Attempts to convert this melt by spray drying, flaking or granulation into a particulate product which flows freely at normal temperature resulted in the formation of tacky, moisture-sensitive materials. In addition, the unreacted residual fatty alcohol still present in the product is noticeable by its unpleasant taste where the alkyl glucosides are used in oral and dental hygiene preparations. However, oral and dental hygiene preparations represent a preferred application for surface-active alkyl glycosides by virtue of their compatibility with mucous membrane.

Accordingly, the problem addressed by the invention was to convert surface-active alkyl glycosides into a pourable, free-flowing form in which they could readily be stored, transported, distributed and incorporated without difficulty in other products, particularly in oral and dental hygiene preparations.

Accordingly, the present invention relates to powder-form preparations of surface-active alkyl glycosides which are characterized in that the contain 5 to 65% by weight of a surface-active alkyl glycoside and 35 to 95% by weight of an inert support and which are obtained by drying of a pourable, aqueous mixture of crude alkyl glycoside and support.

In the context of the invention, a crude alkyl glycoside is understood to be the crude product obtained in the known production process with the secondary constituents attributable to the process, more particularly the reaction mixture containing 2 to 5% by weight unreacted fatty alcohols obtained by the acetalization process described above.

Suitable supports are any chemically and physiologically inert, inorganic support materials which show a substantially neutral or, at best, mildly basic reaction in water and which accumulate in powder form after drying. Particularly preferred supports are substances which are not troublesome when used in oral and dental care preparations, for example in toothpastes, for example because they are already required in another capacity in such preparations. Suitable supports of this type are, for example, the known polishing agent components, such as chalk, silicas, dicalcium phosphate, calcium pyrophosphate, insoluble sodium metaphosphate, aluminium oxide and aluminium oxide hydrates. However, neutral and physiologically acceptable water-soluble salts, such as for example sodium chloride or sodium sulfate, or mixtures of two or more of these supports are also suitable. Other suitable inert supports are alumosilicates, for example layer silicates, talcum, zeolites, magnesium aluminium silicate (Veegum ®), calcium sulfate, magnesium carbonate or magnesium oxide.

Particularly preferred supports are silicas which, by virtue of their large inner surface, give a good free-flowing preparation in small quantities of from about b 0.5 part by weight per part by weight alkyl polyglycoside. With other supports, for example chalk and sodium chloride and sodium sulfate, the ratio by weight of support to alkyl glycoside should be at least 1:1 and, better still, from 1 to 4:1 in order to obtain preparations combining favorable performance properties with an adequate storage life. Accordingly, preferred preparations according to the invention contain 20 to 50% by weight of a surface-active alkyl glycoside and 50 to 80% by weight of an inert, inorganic support.

The finely divided abrasive silicas already used as polishes for toothpastes are preferably used as supports. These silicas are, for example, the precipitated silicas which are known from DE 31 14 492 and DE 31 14 493 or from DE 24 46 038 and which are commercially available; the water-containing gel silicas known from DE 27 04 504 and DE 28 53 647 and the xerogel silicas known, for example, from U.S. Pat No. 3,538,230. However, thickening silicas and pyrogenic silicas, for example Aerosil, may also be used either on their own or in conjunction with other silicas in cases where particularly low powder densities are required.

The physical and performance properties of the powder-form preparations according to the invention may be controlled within wide limits through the choice of the type and quantity of support and through combinations of different supports. For preparations which are to be suitable as an additive for toothpastes and which contain a water-insoluble abrasive as support, the particle size of the support should be largely below $50\mu$ and, on average, should preferably be from 0.1 to $10\mu$.

The preparations according to the invention are produced by mixing 5 to 65 parts by weight of a crude alkyl glycoside obtained in industrial production with 35 to 95 parts by weight of an inorganic support and such a quantity of water that a mixture which still flows freely at a temperature below +80° C. is formed and then removing the water from this mixture by evaporation to such an extent that a powder-form, free-flowing product is obtained. The 30 to 60% aqueous paste of the alkyl glucoside obtained after bleaching of the crude alkyl glucoside by the process according to German patent application P 38 33 780.0 may also be introduced into this mixture. It has been found to be favorable to use approximately 1.5 to 4 parts by weight water to 1 part by weight solid in the production of this mixture. This mixture is generally a paste or slurry which shows poor flow at normal temperature which can be converted by heating to temperatures of up to 80° C. into a readily pumpable and sprayable form. The water-soluble constituents are largely dissolved or swollen in the paste while the water-insoluble components are stably dispersed therein.

The water may be removed from the mixture, i.e. the paste or slurry can be dried, in any way, for example on cylinder or belt dryers, in a fluidized bed of already formed preparation or by spraying into a hot air stream. The last process, so-called spray drying, is the preferred embodiment for the drying of the preparations according to the invention. The water is removed to such an extent that a powder-form, free-flowing product is formed. In most cases, this is the case with water contents of less than 1% by weight. In the cases where the support binds part of the water as water of crystallization, this recommended residual water content is based on the free water which is not bound in the crystal lattice. In cases where relatively large agglomerates are formed during drying, for example on cylinder and belt dryers, it may be necessary to disintegrate these agglomerates in a following grinding step. Where the water is removed by spray drying, the preparations according to the invention do not have to be subsequently disintegrated. For use in toothpastes, the preparations according to the invention should not contain any agglomerates larger than 200μ in diameter while the average primary particle size should be no more than 50μ.

The preparations according to the invention flow freely and remain free-flowing in storage, even in moist air. Another advantage of the powder-form preparations is that the content of residual fatty alcohol is greatly reduced by the production process according to the invention. Accordingly, the preparations may also be used for the production of oral and dental hygiene preparations without any adverse effect on their taste.

The following Examples are intended to illustrate the invention without limiting it in any way.

EXAMPLES

Mixtures according to Table I were prepared from the following raw materials. Mixture No. 1 was spray-dried under the following conditions in a spray-drying tower:

| Drying air: | quantity: | 600 m³/h |
| --- | --- | --- |
| | entry temperatuure: | 170° C. |
| | exit temperature | 155° C. |
| Spray nozzle: | two-component nozzle, 1 mm diameter | |
| Slurry pressure | 4.0 bar | |

-continued

| Spraying air: | 4.0 bar |
| --- | --- |

A fine white powder having excellent flow properties (angle of repose 24.7°) and a residual moisture content of 0.24% by weight $H_2O$ was obtained. The powder had a particle size of 1 to 180μ with maxima at 8μ (primary particle) and 100μ (agglomerate). Mixtures Nos. 2-7 were dried in a laboratory rotary evaporator. Free-flowing, non-tacky powders were again obtained.

Raw materials:
A) alkyl glucoside of a linear $C_{12-14}$ fatty alcohol prepared in accordance with patent application P 38 33 780, Example 3, containing:
  3.0% by weight residual $C_{12-14}$ fatty alcohol
  62.8% by weight alkyl monoglucoside
  15.4% by weight alkyl diglucoside
  5.8% by weight alkyl triglucoside
  2.5% by weight alkyl tetraglucoside
  1.1% by weight alkyl pentaglucoside
  0.2% by weight alkyl hexaglucoside
  6.0% by weight polyglucose
  less than 1.0% by weight glucose
  less than 2.0% by weight salts
B) Sodium chloride
C) Sodium sulfate, anhydrous
D) Chalk (Schäfer Kreide N)
E) Precipitated silica (Siden 12 SPLS, Degussa)
F) Precipitated silica (Sipernat 22 LS 22 SL, Degussa)

TABLE I

| Mixture No. | 1 | 2 | 3 | 4 | 5 | 6 | 7 |
| --- | --- | --- | --- | --- | --- | --- | --- |
| Alkyl glucoside S | 10 | 15 | 10 | 5 | 15 | 10 | 10 |
| Sident 12 SPLS | 20 | 15 | — | — | — | — | — |
| Sipernat 22 LS | — | — | 10 | 10 | — | — | — |
| Schafer Kreide N | — | — | — | — | 30 | — | — |
| NaCl | — | — | — | — | — | 20 | — |
| Na$_2$SO$_4$ | — | — | — | — | — | — | 20 |
| Water | 70 | 70 | 80 | 85 | 65 | 70 | 70 |

In all the powders obtained by spray drying, the contents of residual $C_{12-14}$ fatty alcohol and the residual water content were below 1% by weight.

We claim:
1. A powder-form preparation of surface-active alkyl glucosides, useful in an oral hygiene preparations, consisting essentially of 5%–65% by weight of surface-active alkyl glucosides, wherein the alkyl group contains from 8 to 22 carbon atoms and 35%–95% by weight of at least one inert support, having a median particle size between 0.1 and 10 μm, selected from the group consisting of silica, dicalcium phosphate, calcium pyrophosphate, water-insoluble sodium metaphosphate, aluminum oxide, and aluminum oxide hydrate.

2. A powder-form preparation of claim 1 containing less than 1% by weight of water.

3. A powder-form preparation of claim 1, which contains 20% to 50% by weight of the surface-active alkyl glucoside and 50% to 80% by weight of the inert support.

4. A powder-form preparation of claim 1 obtained by drying an aqueous mixture comprising the alkyl glucoside and the support.

5. A composition of claim 1 wherein the support comprises silica.

* * * * *